US00PP17843P3

(12) United States Plant Patent
Hunter et al.

(10) Patent No.: US PP17,843 P3
(45) Date of Patent: Jul. 3, 2007

(54) PEAR TREE NAMED 'HW610'

(50) Latin Name: *Pyrus communis L.*
Varietal Denomination: HW610

(75) Inventors: David Michael Hunter, St. Catharines (CA); Frank Kappel, Summerland (CA); Harvey Allen Quamme, Penticton (CA); William Gordon Bonn, Windsor (CA)

(73) Assignee: Agriculture and Agri-Food Canada, Harrow, Ontario (CA)

( * ) Notice: Subject to any disclaimer, the term of this patent is extended or adjusted under 35 U.S.C. 154(b) by 202 days.

(21) Appl. No.: 10/190,391

(22) Filed: Jul. 3, 2002

(65) Prior Publication Data

US 2004/0010827 P1 Jan. 15, 2004

(51) Int. Cl.
*A01H 5/00* (2006.01)

(52) U.S. Cl. ..... Plt./176

(58) Field of Classification Search ..... Plt./176
See application file for complete search history.

*Primary Examiner*—Kent Bell
(74) *Attorney, Agent, or Firm*—Flynn, Thiel, Boutell & Tanis, P.C.

(57) ABSTRACT

A new and distinct variety of pear tree, which has been given the designation 'HW610', which produces a high quality, attractive mid-season fruit and has a good to very good rating for quality of fresh and processed fruit.

1 Drawing Sheet

Genus and species: *Pyrus communis L.*

FIELD OF THE INVENTION

The present invention relates to a pear variety and more specifically to a mid-season pear variety for the fresh market.

BACKGROUND OF THE INVENTION

The variety 'HW610', developed by Agriculture and Agri-Food Canada Canada at Harrow, Ontario. The variety has been described by Hunter et al., HortScience, Vol. 37(1):227–229. February 2002. It will be marketed under the brand name AC HARROW CRISP.

SUMMARY OF THE INVENTION

The new and distinct pear variety, which has been given the designation of 'HW610'produces a high quality mid-season pear. The fruits of 'HW610' matured at the end of August or early September just after 'Bartlett' (unpatented). The fruits are also very attractive with a red blush on a smooth yellow skin (RHS 11A–11B). A R.H.S. Color Code that adequately describes the blush color could not be identified. The blush color is a reddish blush where fruits are exposed to the sun. However, this blush is not complete, and interaction with the underlying ground color results in a range of colors which the eye perceives as 'red'. Blush and background color were measured on each fruit using a tri-stimulus colorimeter (Minolta CR-300, Minolta, Toronto, Canada). Fruit chromaticity was recorded in the L, a*, b* space co-ordinates. Fruits had been harvested at maturity, kept in cold storage for approximately 4 weeks, then ripened at room temperature for 3 days. Measurements were made on a sample of 20 fruits, 3 measurements per fruit. The measured values for L, a*, and b* values, together with the calculated values for Chroma (C*) and hue angle (h°), are presented in Table 1. The ground color was rated as RHS 11A–11B. McGuire, R. G. 1992. Reporting of objective color measurements. *HortScience* 27:1254–1255. Voss, D. H. 1992. Relating colorimeter measurement of plant color to the Royal Horticultural Society Colour Chart. *HortScience* 27:1256–1260.

TABLE 1

L, a* and b* space coordinates and calculated Chroma (C*) and hue angle (h°) for Harrow Crisp fruit blush and ground color.

| | Blush colour | | | | |
|---|---|---|---|---|---|
| | L | a* | b* | C* | h° |
| Mean | 61.31 | 8.84 | 33.82 | 35.25 | 75.14 |
| St Dev | 2.18 | 4.12 | 2.82 | 2.01 | 7.43 |
| Min | 57.51 | 1.41 | 27.11 | 31.77 | 50.84 |
| Max | 65.68 | 22.08 | 38.72 | 39.24 | 87.89 |
| N | 60 | 60 | 60 | 60 | 60 |
| | **Ground colour** | | | | |
| | L | a* | b* | C* | h° |
| Mean | 73.71 | −3.89 | 42.87 | 43.09 | 95.14 |
| St Dev | 1.85 | 1.91 | 1.6 | 1.67 | 2.48 |
| Min | 68.6 | −8.43 | 39.31 | 39.33 | 86.95 |
| Max | 77.56 | 2.11 | 45.78 | 45.99 | 101.09 |
| N | 60 | 60 | 60 | 60 | 60 |

The cream-white (RHS 11D–158C) flesh is smooth, grit free, and remains firm even when fruits are fully ripe. Fruits of 'HW610' have a mild, sweet flavor that is less intense than that of 'Bartlett', (unpatented). Fruit size on unthinned trees is slightly larger than 'Bartlett'. It has a good to very good rating for quality of both fresh and processed fruit. The tree of 'HW610' is medium in size, conical and upright, annually productive and hardy. The tree has very good fire blight resistance (9.5 rating, similar to "Harrow Delight', ('unpatented') compared to 'Bartlett' (4.2 rating). The response to infection following inoculation with the causative organism is more severe in 'Bartlett' (mean lesion length 63% of shoot length, with some lesions extending into subtending woody tissues) than in 'HW610' (mean lesion 12% of shoot length, maximum lesion length 32% of shoot length).

DETAILED DESCRIPTION OF THE VARIETY

Figure 1:
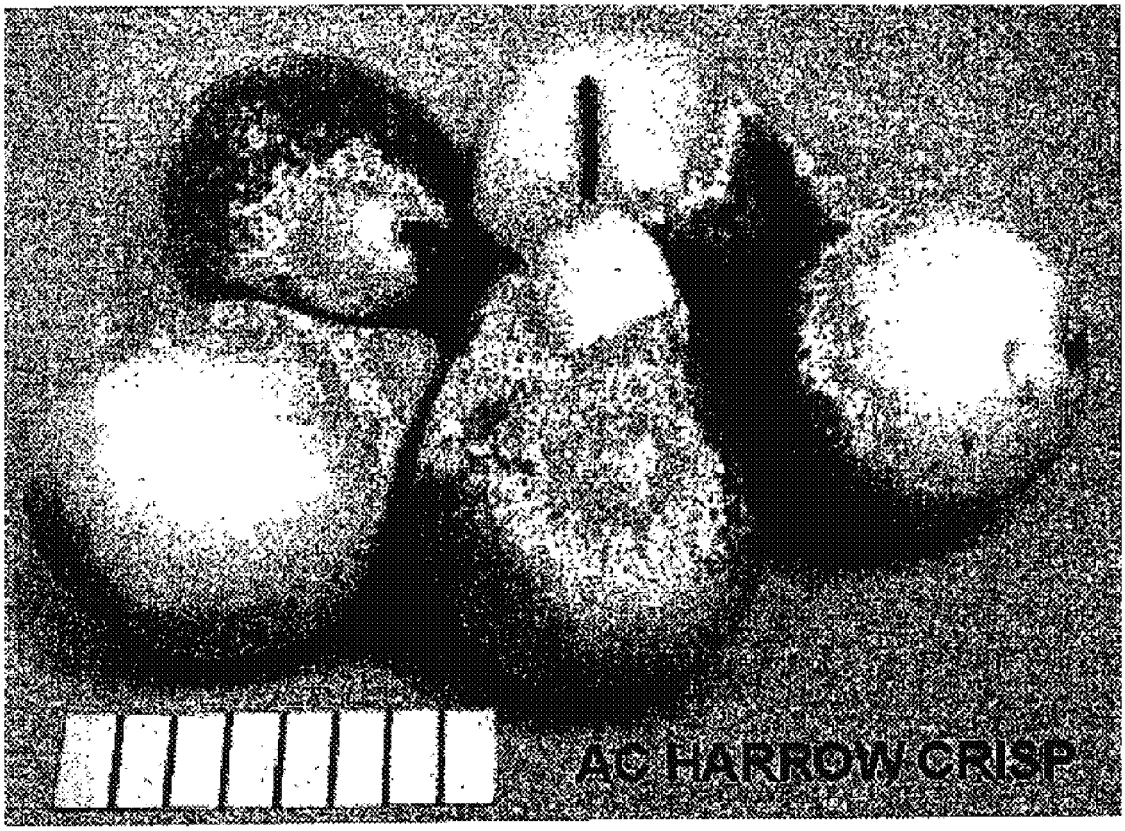
FIG. 1 is a photographic illustration of the whole fruit of 'HW610'. The fruits depicted in FIG. 1 were obtained from mature (~10 years old) trees of the variety grown on 'Bartlett' seeding rootstock at the AAFC Research Centre, Harrow, Ontario, Canada. These are the same trees that were used to obtain the botanical description data.

'HW610' resulted from a controlled cross between 'Bartlett' and 'US56112-146' ('unpatented') made in 1972 by Dr. H. A. Quamme at the Agriculture and Agri-food Canada Research Centre at Harrow, Ontario. It was selected as a hybrid seedling 'H7249-A-32' (unpatented) in 1979 by H. A. Quamme, and propagated by budding on pear seedling rootstocks. It was advanced by H. A. Quamme in 1981, and testing began in 1982 at the Harrow Research Centre. Propagation for regional trials in cooperation with the Western Ontario Fruit Testing Association began in 1982, and test trees were placed in regional trials beginning in 1984. Evaluations of second test orchards have been conducted by F. Kappel and D. M. Hunter, and W. G. Bonn has evaluated disease resistance.

Asexual propagation maintains uniformity and stability of 'HW610'. No variants, off-types or mutants have been observed. The variety will be maintained at the Agriculture and Agri-Food Canada Harrow Research Centre in a virus-tested budwood orchard, and in the holdings of the Canadian Clonal Genebank.

The color terminology is in accordance with The Royal Horticultural Society (R.H.S.) Color Chart.

Tree habit and productivity. The tree of 'HW610' is medium in size, conical and upright, annually productive, and winter hardy. In 1994 at Harrow, the original seedling tree and trees grown on 'Bartlett' seedling rootstock produced a full crop following winter minimum temperatures as low as −29° C. When propagated on 'Bartlett' seedling rootstock, precocity of 'HW610' is similar to that of 'Bartlett', with bearing initiated with a 4-year period after planting. Annual yields have been greater than those of 'Bartlett', especially in areas where fire blight has adversely affected the productivity of 'Bartlett'. In an evaluation orchard planted in 1982 at Harrow, 'HW610' produced commercially acceptable crops until the orchard was removed in Fall 2000 (data not presented), while all 'Bartlett' trees had been removed by 1990 because of extensive fire blight damage. 'HW610' out-yielded 'Anjou' (unpatented) and 'Bosc' (patented), in the first 5 years of an orchard planted at Summerland, B.C. (Table 2).

TABLE 2

Annual fruit yields of 'HW610', 'Anjou', 'Bosc' (U.S.P.P. 7485), and 'Harrow Sweet' ('U.S.P.P. 9863') at Summerland, B.C., Canada.

| | Annual yield (kg/tree) | | | | | Cumulative |
|---|---|---|---|---|---|---|
| Cultivar | 1989 | 1990 | 1991 | 1992 | 1993 | yield (kg/tree) |
| 'HW610' | 7.6a[y] | 4.3ab | 18.7a | 12.5a | 21.4ab | 64.5 |
| 'Anjou' | 1.2c | 2.4b | 9.4a | 3.9b | 27.8ab | 44.7 |
| 'Bosc' | 3.2b | 4.5ab | 16.5a | 13.6a | 20.1b | 57.9 |
| 'Harrow Sweet' | 7.7a | 8.1a | 16.4a | 5.4b | 32.7a | 70.3 |

[z]Orchard was planted in 1987 with five single tree replicates in a completely randomized design.
[y]Means separation within columns by Waller-Duncan K ratio t test, P = 0.05. Means within columns followed by the same letter are not significantly different.

Shoot. The bark on the sun-exposed side of dormant shoots is brown (RHS 165A, 1966). Mean internode length of 'HW610' was similar to 'Bartlett' and 'Harrow Sweet', but shorter than 'Harvest Queen' (unpatented) and 'Bosc' (Table 3).

TABLE 3

Mean internode length (cm ± SE) as determined on five successive internodes from the mid-portion of 1-year-old shoots[Z]

| Cultivar | Internode length | No. of Shoots |
|---|---|---|
| 'HW610' | 3.1 ± 0.1 | 19 |
| 'Bartlett' | 3.3 ± 0.1 | 13 |
| 'Harrow Sweet' | 3.1 ± 0.1 | 15 |
| 'Harvest Queen' | 3.7 ± 0.2 | 17 |
| 'Bosc' | 4.4 ± 0.1 | 14 |

[Z]Shoots harvested in Feb. 1996 from mature trees (>10 years old) grown on 'Bartlett' seedling rootstock at Harrow, Ont., Canada.

Leaves. The leaves are elliptic. The shape of the base of the leaf blade is obtuse. The shape of the upper part of the leaf blade is right-angled, with a pointed acuminate tip. There is little curvature of the midrib. Leaf serrations are small and shallow but distinct. The angle between the petiole and the shoot is <30%, the petiole is medium in length, and stipules are absent. The attitute of the leaf in relation to the shoot is upwards. Actively growing shoot tips are reddish-green with light pubescence.

Leaf size data from these trees are presented in Table 4.

TABLE 4

Mean (mm ∀ SE) leaf length, width and petiole length as determined on leaves collected from the mid-portion of current season's extension growth[Z]

| 'Cultivar' | Leaf length | Leaf width mm | Petiole length |
|---|---|---|---|
| 'HW610' | 61.6 (8.8) | 37.6 (5.6) | 20.4 (5.4) |
| 'Bartlett' | 67.0 (7.3) | 39.1 (5.2) | 17.8 (5.7) |
| 'Harrow Delight' | 74.9 (6.9) | 37.5 (4.0) | 19.8 (3.1) |
| 'Harvest Queen' | 65.6 (8.6) | 34.7 (7.1) | 23.0 (10.3) |
| 'Bosc' | 69.5 (11.9) | 43.0 (11.9) | 19.0 (8.9) |

[Z]Leaves (1 leaf/shoot, 10 shoots/tree, 4 trees/cultivar, n = 40) were harvested Jul. 27, 1995 from mature trees (>10 years old) grown on 'Bartlett' seedling rootstock at Harrow, Ontario, Canada.

The adaxial surface of leaves of HW610 obtained from the mid-section of current season's extension growth from trees (~10 years old) grown on 'Bartlett' seedling rootstock at the AAFC Jordan Farm, Jordan Station, Ontario, Canada, was described using The Royal Horticultural Society Color Chart as 137A, while the abaxial surface was described as 147B. Both adaxial and abaxial leaf surfaces were described as smooth.

Flowers. At Harrow, Ontario, Canada, the date of first bloom of HW610 is about May 8 (depending on season), later than 'Harrow Delight' (~May 4), 'Harvest Queen' and 'Bartlett' (~May 6) and similar to 'Bosc' (~May 8). The date of full bloom is ~May 13, similar to 'Bartlett', later than 'Harrow Delight' and 'Harvest Queen' (~May 11) and earlier than 'Bosc' (~May 14). Flower descriptive data obtained at ~ full bloom are presented in Table 5.

TABLE 5

Flower characteristics of 'HW610' in comparison to 'Harrow Delight', 'Harvest Queen', 'Bartlett' and 'Bosc'.

| Characteristic | 'HW610' | 'Harrow Delight' | 'Harvest Queen' | 'Bartlett' | 'Bosc' |
|---|---|---|---|---|---|
| Pedicel: | | | | | |
| length | medium-long | long | medium-long | medium | long |
| Sepal: | | | | | |
| length | medium-long | long | short-medium | medium | long |
| position | horizontal-recurved | horizontal-recurved | horizontal-recurved | horizontal | recurved |
| Petals: | | | | | |
| overlapping | touching | separate-touching | separate | separate-touching | widely separate |
| length (inc. claw) | short-medium | medium-long | medium | medium | very long |
| length/breadth | long broad | longer > broad | long broad | long broad | longer >> broad |
| shape of base (ex. claw) | u-shaped | v-shaped | u-shaped | flat or cordate | v-shaped |
| length of claw | short-medium | medium-long | short-medium | short-medium | short |
| undulation of margin | strong | medium | medium | medium | medium-strong |
| Stigma: | | | | | |
| position as compared with anthers | level-above | level | level | below | above |
| Anther: | | | | | |
| size | large | medium-large | medium-large | medium | medium |
| Receptacle: | | | | | |
| shape | slightly hollowed | hollowed | hollowed | hollowed | slightly hollowed |

Fire blight resistance. As with other introductions from the Harrow pear breeding program (Hunter et al., 1992, 2002; Quamme and Spearman, 1983), 'HW610' has excellent resistance to fire blight, similar to or greater than that of 'Kieffer' (unpatented) which is used as the standard for selection (Hunter, 1993). Using natural fire blight infection scores (van der Zwet et al., 1970), 'HW610' had a resistance rating much greater than 'Bartlett' as is shown in Table 6.

| | 'HW610' | 'Bartlett' | 'Harrow Sweet' | 'Kieffer' |
|---|---|---|---|---|
| | Natural infections[z] | | | |
| Rating | 9.5 ± 0.2 | 4.2 ± 0.4 | 9.2 ± 0.2 | 9.3 ± 0.1 |
| Years evaluated | 13 | 18 | 17 | 15 |
| | Induced infections[y] | | | |
| Lesion (% shoot length) | 11.8 ± 3.0 | 62.8 ± 4.2 | 14.1 ± 2.5 | 23.1 ± 1.6 |
| Years evaluated | 11 | 22 | 11 | 16 |

[z]Natural fire blight infections, rated on a scale of 1 (tree dead) to 10 (no blight), are means ± SE of 13 to 18 years at Harrow, Ont., Canada. The rating system was modified from van der Zwet et al. (1970) by assigning values of 10 = no visible blight and 9 = <3% infection. For 'HW610' and 'Harrow Sweet', ratings were made on the own-rooted seedling tree. For 'Bartlett' and 'Kieffer', ratings were made on trees grown on 'Bartlett' seedling rootstock in a nearby (within 200 m) cultivar evaluation orchard. In both the seedling orchard and the cultivar evaluation orchard, susceptible trees had severe fire blight infections each year.
[y]Induced infections were rated in late July, ≈5 weeks after inoculating 10–20 actively growing shoots with 20 μL of a cocktail of six virulent strains of *Erwinia amylovora* ($10^8$ cfu/mL). Values indicate lesion length expressed as a percentage of total shoot length. Data are means ± SE of 11 to 22 years.

When actively growing shoot tips were inoculated with a mixture of six virulent strains of *E. amylovora,* the length of the lesion that developed extended to ≈12% of current season's growth, similar to 'Harrow Sweet' (patented) and 'Kieffer', but much less than lesion development in 'Bartlett' (Table 6).

Bloom and pollination. At Harrow, the time of full bloom of 'HW610' is similar to that of 'Bartlett'. First bloom, however, is 2 days later than 'Bartlett'. Flower clusters typically contain seven flowers, occasionally six or eight, rarely five or nine. Petals are white (RHS 155B or 155D), almost as long as broad, and just touch with no overlap. The anthers are pink-red (RHS 54A–54B) anthers are large in size, and are level with or slightly above the stigma. 'HW610' tends to be a poor pollinizer.

In controlled pollination tests, fruit set was used to determine pollen compatibility when pollen from a known source was applied to stigmatic surfaces immediately after emasculation of the flower. Because emasculated pear flowers are even less attractive to bees and other pollinating insects than nonemasculated flowers, bagging was not considered necessary. 'HW610' will not consistently pollinate 'Bartlett', 'Bosc', or 'Anjou', especially when spring weather is warm and humid; however, under the cooler conditions experienced in Spring 2000, 'HW610' pollinated 'Bartlett', 'Bosc', 'Anjou', 'Flemish Beauty', and 'HW616', but these cultivars did not adequately pollinate 'HW610'. Also in 2000, pollination of emasculated flowers of 'HW610' with pollen of 'HW610' resulted in adequate fruit set for commercial production. Seed set in 'HW610' tends to be low, and large-sized fruits can develop with few or no viable seeds.

Fruit characteristics

Size, shape, and color. Fruits are slightly larger than 'Bartlett' (Table 7).

TABLE 7

Harvest dates at Harrow, Ont., Canada, and fresh fruit evaluations for 'Bartlett', 'HW610', and 'Harrow Sweet'.

| | 'Bartlett' | 'HW610' | 'Harrow Sweet' |
|---|---|---|---|
| Years evaluated | 20 | 17 | 18 |
| Harvest dates | | | |
| Average | 28 Aug. | 3 Sept. | 18 Sept. |
| Earliest | 18 Aug. | 22 Aug. | 29 Aug. |
| Latest | 9 Sept. | 27 Sept. | 8 Oct. |
| Size (mm) | | | |
| Length | 81.4a[Z] | 84.4a | 84.6a |
| Diameter | 63.4a | 65.1a | 63.5a |
| Ratings[Y] | | | |
| Appearance[X] | 7.7b | 8.6a | 7.4b |
| Flavor[X] | 8.0a | 7.4b | 7.8ab |
| Texture[X] | 7.9a | 7.4ab | 7.1b |
| Weighted score[W] | 81.3a | 79.4ab | 77.1b |
| Grit[V] | 3.9a | 4.2a | 3.1b |
| Juice[U] | 3.9a | 3.1b | 4.2a |
| Core[t] | 3.2b | 3.0b | 3.8a |

[Z]Means separation within rows by Duncan's new multiple range test, P = 0.05. Means within rows followed by the same letter are not significantly different.
[Y]Ratings reported are based on evaluations of fruits ripened immediately after harvest.
[X]Appearance, flavor and texture ratings [on a scale of 1 (least desirable) to 9 (most desirable)] were determined each year by two to four trained panelists.
[W]Weighted score = (3 × appearance) + (5 × flavor) + (2 × texture).
[V]Grit rating is on a scale of 1 (undesirable, i.e. large and/or many grit cells) to 5 (desirable, i.e., very small and/or few or no grit cells).
[U]Juiciness rating is on a scale of 1 (dry) to 5 (very juicy).
[t]Core size rating is on a scale of 1 (small) to 5 (large).

Fruit shape is symmetrical, pyriform, and concave to almost straight in profile. Using International Board for Plant Genetic Resources descriptors (Thibault et al., 1983), the predominant fruit shape has been described as 5.2 (≈50% of individual fruits), while other individual fruits have been described as 5.4 (≈25%) or 7.2 (≈20%). The calyx is persistent at harvest, with short to medium length sepals that are convergent to upright. The calyx basin is medium length and narrow to medium in width, and the margin is even to slightly ribbed. Following ripening at ≈20° C., the skin has a very attractive golden yellow ground color (RHS 11A or 11B) with a red blush (Table 1) on the sun-exposed fruit surface. The skin is very smooth and there is little or no russeting of the fruit. The flesh is white to cream-white in color, very fine in texture, grit-free, and remains firm even when fully ripe. Fruits have a mild sweet flavor and relatively little juice.

Pre-harvest drop is not a problem with HW610.

Height and circumference measurements and description of the calyx basin are presented in the application.

The stem is straight to slightly curved, the insertion is oblique to the fruit axis, and the cavity is shallow. The length of the fruit stem is rated medium-long, longer than 'Harrow Delight' (unpatented), rated short and 'Bartlett' (rated short-medium), but shorter than 'Bosc' (rated long).

The diameter of the fruit stem is rated thin-medium, thinner than 'Harrow Delight', 'Bartlett' and 'Bosc' (all rated medium) and 'Harvest Queen' (rated thick).

Seed color for mature, air dried seeds is predominantly RHS 200A, with some 200B. Seeds freshly extracted from fruits harvested at maturity, kept in cold storage for approximately 4 weeks, then ripened at room temperature for 3 days, seed color was predominantly RHS 200A, occasionally with lighter colored areas at the tip (RHS 166C–166D). When air-dried, these seeds were rated RHS 200A and 200B. The seed shape is elongated rather than egg-shaped, and size is medium large. Although, fruits typically have five (5) elongated carpels, seed numbers are low (often less than five sees per fruit), and it is not uncommon to have fruits with no viable seeds. These seeds were collected in the fall of 2005, air-dried in the lab, then stored in a cooler at 40 degrees C. and lower humidity.

Maturity. At Harrow, Ont., Canada, the fruits of 'HW610' mature at the end of August or early September, just after 'Bartlett' (Table 7), and can be harvested over a 2-week period. Early picked fruits can be stored in common cold storage (1 to 2° C.) for ≈2 months, but storage life is reduced with later picking. Core breakdown can be a problem with overripe fruits.

Quality. At Harrow, fruits were harvested each year at the normal fresh market maturity for commercial harvest (5–7 kg pressure). Following ripening at ≈20° C. until 'eating ripe', a sample of 5–10 fruits, selected at random, was evaluated for appearance, flavor, texture, number and size of grit (stone cells) in the flesh, juiciness, and core size relative to fruit size. Evaluations were made on fruits ripened immediately after harvest. At Harrow, trained panelists rated the appearance of ripened fruits of 'HW610' as excellent, and significantly better than 'Bartlett' and 'Harrow Sweet'. Fresh fruit quality of 'HW610', as indicated by the weighted score, was intermediate between, but not statistically different from, 'Bartlett' and 'Harrow Sweet' (Table 7). There are no significant differences between fruits ripened immediately after harvest and fruits ripened after 4 weeks in a common cold storage at ≈2° C. (data not presented).

In the $5^{th}$ leaf, trees of HW610 grown on 'Bartlett' seedling rootstock had a trunk cross sectional area (TCSA) of 25.8∀5.8 $cm^2$ (n=5), while 'Bartlett' on 'Bartlett' seedling rootstock in the same planting had a TCSA of 21.6∀5.8 $cm^2$ (n=5). However, 'Bartlett' trees in this planting were already affected by fire blight, and all 'Bartlett' trees were removed by the $9^{th}$ leaf [0008]. No additional data are available for the trees used for botanical description data. Subjective evaluations indicate that trees grown on 'Bartlett' seedling rootstock in a managed orchard are medium in size, and come into production within 4 years of planting (similar to 'Bartlett'). These evaluations suggest that tree vigour and growth rate for trees of HW610 grown on 'Bartlett' seedling rootstock are similar to 'Bartlett'.

Processing evaluations. When ripened fruits are processed as pear halves, 'HW610' remains intact, with virtually no breakdown, and there is no discoloration of the fruit or syrup. 'HW610' rates almost as highly as 'Bartlett', and significantly better than 'Harrow Sweet' (Table 8).

TABLE 8

Ratings of pear halves[z] and pear purée[y] processed from ripened fruits of 'HW610' in comparison with 'Bartlett' and 'Harrow Sweet'

| | 'HW610' | 'Bartlett' | 'Harrow Sweet' |
|---|---|---|---|
| Halves | 3.8a[x] | 3.9a | 3.4b |
| Puree | 3.6b | 4.0a | 3.3b |

[z]Determined with masked identity taste panels involving four trained panelists. Fruits were processed in syrup containing 15% (w/v) sugar. Processing rating for pear halves is the average of ratings for flavor, texture and appearance on a scale of 1 (least desirable) to 5 (most desirable). Samples, including a masked identify 'Bartlett' sample, were compared to a known 'Bartlett' sample. Data presented are means of 5 years.

[y]Determined with masked identify taste panels involving four trained panelists. Fruits were processed with no additional sugar. Processing rating for purée is the average of ratings for viscosity, color, and flavor on a scale of 1 (least desirable) to 5 (most desirable). Samples, including a masked identify 'Bartlett' sample, were compared to a known 'Bartlett' sample. Data presented are means of 5 years.

[x]Means separation within rows by Duncan's new multiple range test, P = 0.05. Means within rows followed by the same letter are not significantly different.

When processed as pear purée, 'HW610' is rated better than 'Harrow Sweet' but not as high as 'Bartlett'. While the processed product from small scale trials has been rated good, the quality may not be sufficiently high for 'HW610' to have commercial acceptability for processing as halves or purée in the current market.

'HW610' was tested at the Canadian Centre for Plant Health, Saanichton, B.C., using woody-host and herbaceous-host biological indicators, and by serological and molecular methods, and found to be free of all known viruses, virus-like agents, viroids, and phytoplasmas. Virus-tested trees have been planted in the Canadian Clonal Gene Bank at Harrow.

It is claimed:

1. A new and distinct variety of pear tree substantially as shown and described herein.

* * * * *